United States Patent [19]
Cooper et al.

[11] Patent Number: 5,800,567
[45] Date of Patent: Sep. 1, 1998

[54] KNEE MECHANISM FOR AN ARTIFICIAL LIMB

[75] Inventors: John Edwin Cooper, Haslemere, Great Britain; Robert E. Arbogast, Mount Sterling, Ohio; Jay H. Kinsinger, Cedarville, Ohio; Sujatha Srinivasan, Mount Sterling, Ohio

[73] Assignee: Ohio Willow Wood Company, Mount Sterling, Ohio

[21] Appl. No.: 816,002

[22] Filed: Mar. 10, 1997

[30] Foreign Application Priority Data

Mar. 11, 1996 [GB] United Kingdom ............... 9605110

[51] Int. Cl.⁶ ............................................. A61F 2/62
[52] U.S. Cl. ........................ 623/39; 623/43; 623/46
[58] Field of Search ....................... 623/39, 40, 41, 623/42, 43, 44, 45, 46

[56] References Cited

U.S. PATENT DOCUMENTS

| | | | |
|---|---|---|---|
| 2,208,275 | 7/1940 | McCann et al. | 623/39 |
| 2,638,605 | 5/1953 | Johnson | 623/39 |
| 3,823,424 | 7/1974 | May | 623/39 |
| 4,310,932 | 1/1982 | Näder et al. | |
| 4,723,539 | 2/1988 | Townsend | 623/39 X |
| 4,756,712 | 7/1988 | Clover, Jr. | 623/39 |
| 5,376,137 | 12/1994 | Shorter et al. | 623/46 |
| 5,545,232 | 8/1996 | Van de Veen | 623/39 |
| 5,632,725 | 5/1997 | Silver et al. | 623/39 X |

FOREIGN PATENT DOCUMENTS 1533796  11/1978  United Kingdom ............... 623/39

*Primary Examiner*—Mary Beth Jones
*Attorney, Agent, or Firm*—Oblon, Spivak, McClelland, Maier & Neustadt, P.C.

[57] ABSTRACT

A knee mechanism for a lower limb prosthesis which maintains knee stability over an initial range of flexion and includes an upper member for connection to or forming part of the thigh component of a prosthesis, a lower member for connection to or forming part of the shin component of a prosthesis, and a slider and a crank connecting the upper member to the lower member. The locus of the instantaneous center of rotation of the mechanism is a curve which commences above the knee and posterior to the load line and which, over an initial range of flexion of the mechanism, moves continuously downwards and to the posterior, the curve being convex towards the posterior. The lower member, the slider and the crank preferably constitute a slider crank mechanism with the crank pivotally connected to the upper and lower members and the slider pivotally connected to the lower member and slidably connected to the upper member. At full extension the crank is inclined posteriorly and upwardly, with the pivotable connection with the upper member located below the pivotable connection with the lower member. The slider is located in a track which forms part of the upper member and may move with a rolling or sliding contact. The pivotal connection of the slider with the lower member is located posterior to the pivotal connection with the crank.

34 Claims, 4 Drawing Sheets

KNEE MECHANISM FOR AN ARTIFICIAL LIMB

BACKGROUND OF THE INVENTION

1. Field of the Invention

This invention relates to a polycentric knee mechanism for a lower limb prosthesis and to a prosthesis including the mechanism.

2. Description of the Related Art

The use of polycentric knee mechanisms in artificial limbs is well known. Commonly, such a mechanism comprises a four bar linkage and has an instantaneous center of rotation which is located so as to provide knee stability in the fully extended position. It is also customary to locate the instantaneous center above the knee in order to reduce the moment required to flex the knee when it is weight bearing. Typically, the instantaneous center of rotation moves anterior when the knee commences flexion and knee stability is thereby lost.

SUMMARY OF THE INVENTION

It is an object of this invention to provide an improved polycentric knee mechanism.

According to the present invention there is provided a polycentric knee mechanism for a lower limb prosthesis which maintains knee stability over an initial range of flexion and which comprises an upper member for connection to or forming part of the thigh component of a prosthesis, a lower member for connection to or forming part of the shin component of a prosthesis, and a polycentric linkage including a slider and a crank connecting the upper member to the lower member, wherein the arrangement of the slider and crank is such that the locus of the instantaneous center of rotation of the mechanism, when the lower member is rotated with respect to the upper member, is a curve which commences, at a point corresponding to full extension of the mechanism, above the knee and posterior to the load line and which, over an initial range of flexion of the mechanism, moves continuously downwards and to the posterior with increasing flexion, the curve being convex towards the posterior.

In the preferred embodiment of the invention, the upper member, the lower member, the slider and the crank constitute a slider crank mechanism with the crank pivotally connected to the upper and lower members and the slider pivotally connected to the lower member and slidably connected to the upper member. At full extension the crank is inclined posteriorly and upwardly having the pivotable connection with the upper member located below the pivotable connection with the lower member. The slider is located in a track which forms part of the upper member and may move with a rolling contact or alternatively a sliding contact. The pivotal connection of said slider, in the lower member, is located posterior to the pivotal connection with the crank. The position of the instantaneous center is determined by the intersection of a line perpendicular the track, and passing through the center of the pivotable connection with the lower member, and a line extending from the centers of the pivotable connections of the crank with the upper and lower members. The position of the instantaneous center in the fully extended position determines the level of stability, which may be varied by adjusting the position of the slider track in the upper member.

Means may be provided by which the crank resists torsional loading. The crank may consist of side members which are interconnected by a bridge member rotating with the side members and extending in a medial-lateral direction. The combination of the side members and the bridge member being typically arranged in a "U" configuration.

The invention includes a lower limb prosthesis having a knee mechanism as defined above.

BRIEF DESCRIPTION OF THE DRAWINGS

Specific embodiments of the invention will now be described by way of example with reference to the accompanying drawings in which.

DETAILED DESCRIPTION OF THE PREFERRED EMBODIMENTS

Figure 1:
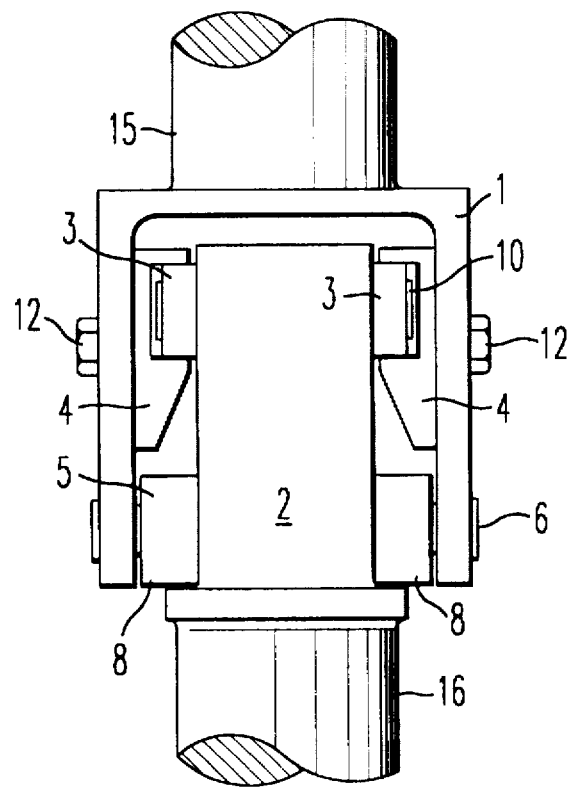
FIG. 1 shows a rear elevation of an embodiment of the knee mechanism in the fully extended position.

The knee joint of the first embodiment illustrated in FIGS. 1–5 comprises an upper member 1, a lower member 2, and a polycentric linkage including sliders 3, tracks 4 and crank 5. The term "sliders" as used herein is broad enough to include rollers and other members capable of guided or confined movement with respect to the tracks 4.

Crank 5 rotates on pins 6 and 7 which are retained in upper member 1 and lower member 2, respectively. Crank 5 has a generally U shape and comprises side members 8 connected by bridge member 9 which provides resistance to torsional loads. The crank extends substantially vertically, and the pivotal connection of the crank 5 with the upper member is below and anterior to the pivotal connection of the crank with said lower member, when the lower member 2 is in a fully extended position.

Sliders 3 roll in tracks 4 and rotate on pin 10 which is retained in lower member 2.

Tracks 4 are attached to upper member 1 by dowels 11 and screws 12 and may be assembled in alternative positions to provide different levels of stability. They generally extend substantially perpendicular to the load line of the upper member.

Sleeve 13 fits over pin 6 and abuts with a suitably shaped cutout in lower member 2 to provide an extension stop, although a stop may be provided by any pair of surfaces between upper member 1, lower member 2 or crank 5.

Figure 2:
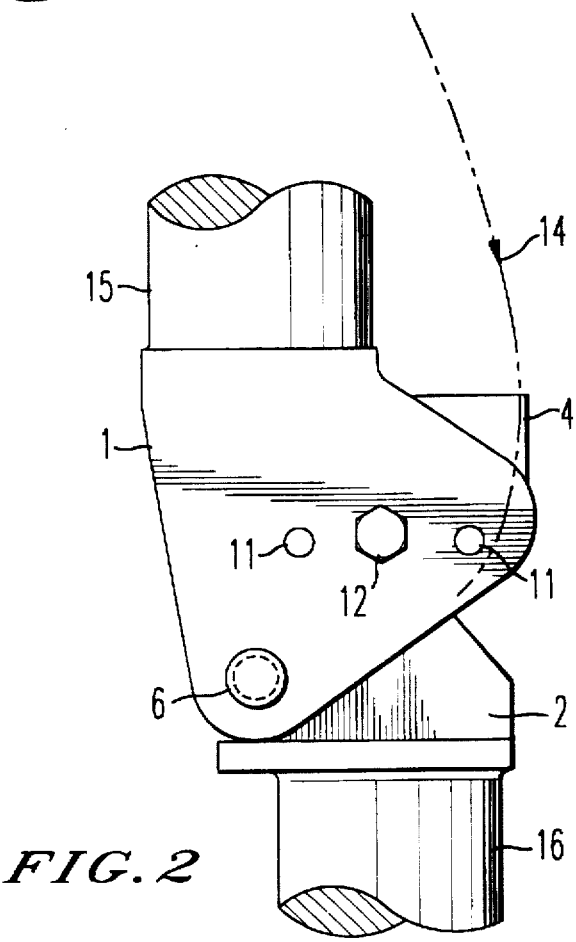
FIG. 2 shows a side elevation of a fully extended knee mechanism of FIG. 1, viewed from the lateral side, with the anterior region to the left of the drawing and the posterior to the right.
Figure 3:
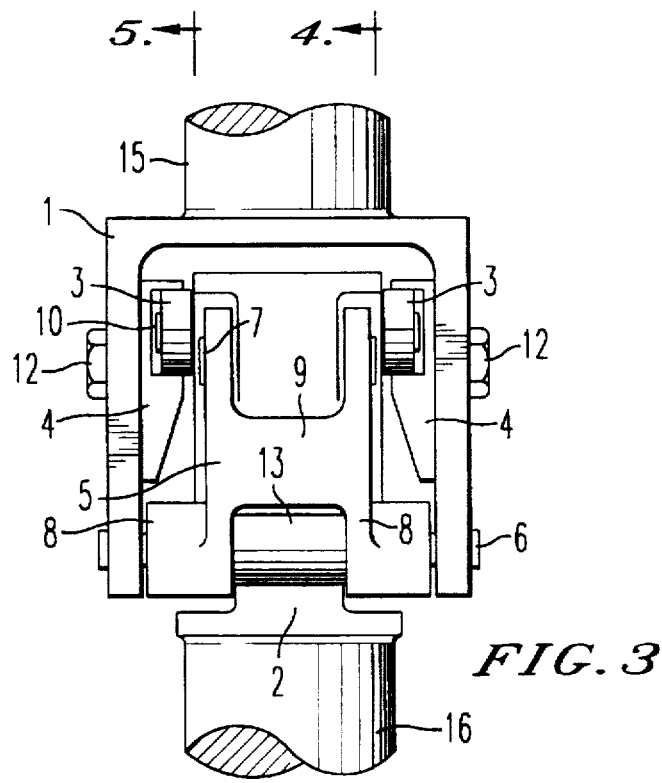
FIG. 3 shows a front elevation of the knee mechanism of FIG. 1 in the fully extended position.
Figure 5:
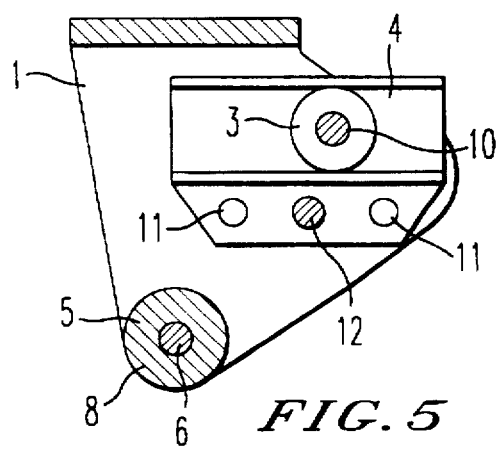
FIG. 5 shows a cross section of the knee mechanism along line 5—5 of FIG. 3.
Figure 4:
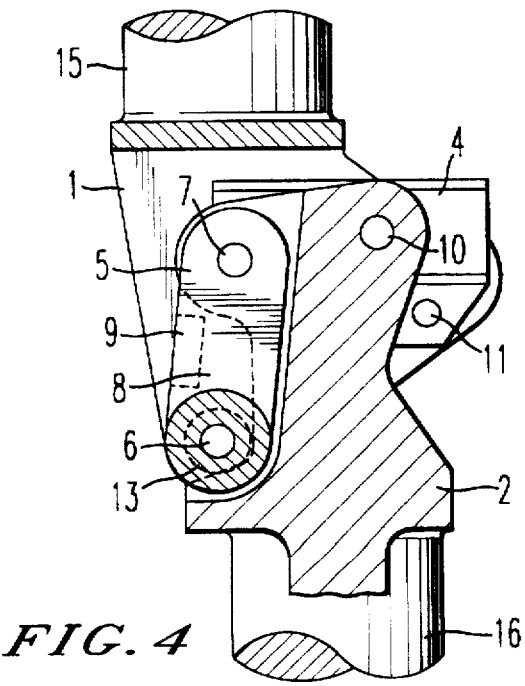
FIG. 4 shows a cross section of the knee mechanism along line 4—4 of FIG. 3.

The chain line 14 of FIG. 2 represents the locus of the path of the instantaneous center of rotation at different positions of the mechanism and the arrowhead shows the direction of movement of the instantaneous center with increasing flexion.

Projections 15 and 16 respectively represent the thigh and shin members of the artificial limb although either member may be connected by a suitable arrangement such as a screw or a set of screws.

Figures 6, 7:
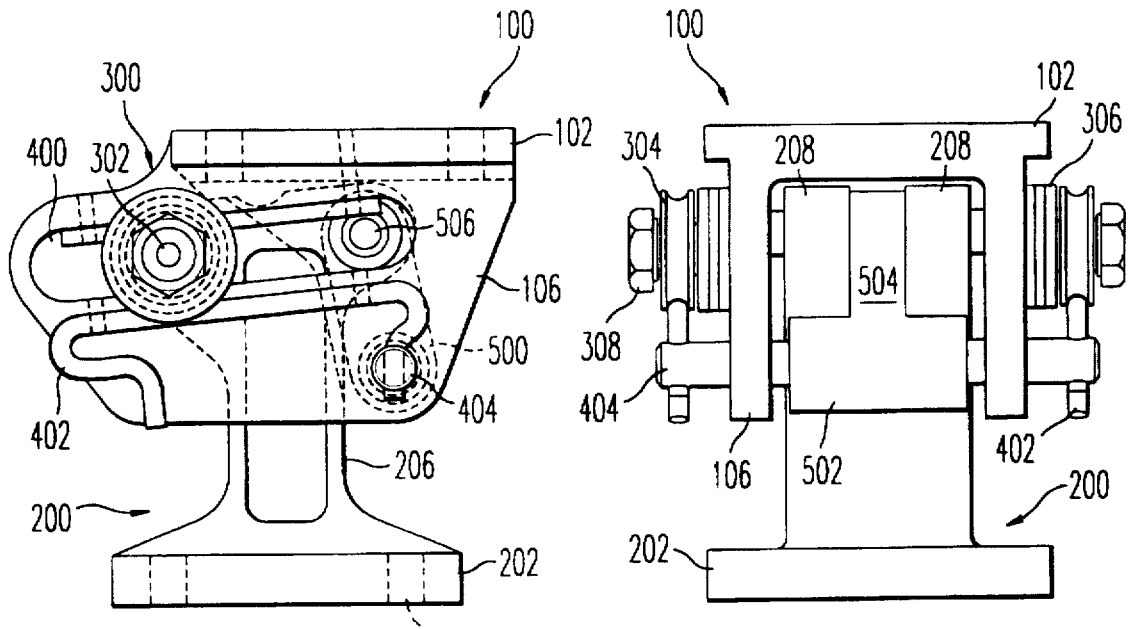
FIG. 6 shows a side elevation of a fully extended knee mechanism of a second embodiment, viewed from the lateral side, with the anterior region to the right of the drawing and the posterior to the left.
FIG. 7 corresponds to FIG. 3 but shows the second embodiment.
Figure 8:
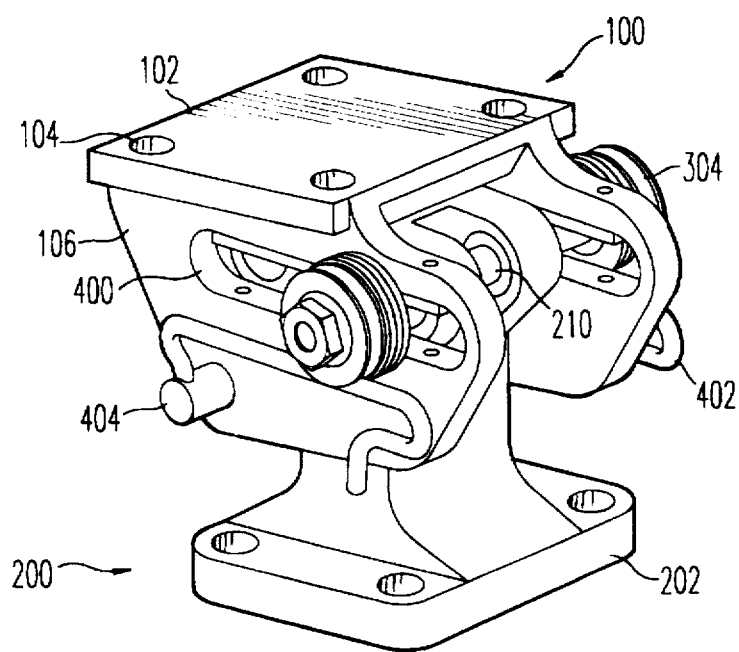
FIG. 8 is a perspective view, from the posterior quarter and from above, of the second embodiment.

Referring now to the second embodiment of FIGS. 6–8, the same reference numbers will be used to designate the same or corresponding parts as those of the first embodiment except that the respective reference numbers will include two additional zeros. The following description will focus on the differences between the embodiments.

The upper member 100 is in the form of a rectangular plate 102 having holes 104 for screws or bolts to be used for attachment to a thigh member of the prosthesis. A pair of depending skirts 106 extend downward from the plate 102 and each includes a track in the form a slot 400.

The lower member 200 has a rectangular base 202 with bolt holes 204. A pedestal 206 extends upwardly from the base 202 and includes a pair of bosses 208, each having a hole 210 forming a journal bearing. The holes 210 are aligned and are positioned between, and are aligned with, the slots 400 when the knee mechanism is in the illustrated fully extended position.

The slider 300 comprises a pin 302 rotatably mounted in the journal bearings of the bosses 208 and extending through the slots 400. The walls of the slots 400 guide and support the pin 302 during flexure of the knee mechanism. A pair of rollers 304 are mounted on opposite ends of the pin 302. Thrust bearings in the form of washers 306 are mounted on the pin 302 between the rollers 304 and the skirts 106. The rollers 304 are held on the pin 302 by nuts 308 threaded onto the ends of the pin.

Anti-rattle spring wires 402 are mounted to the exterior sides of the skirts 106 at positions below and parallel to the slots 400. The wires 402 resiliently press on concave peripheral surfaces of the rollers 304 as the slider 300 moves along the slot 400 during flexion of the knee to prevent rattling of the slider 300 in the slot 400.

The wires 402 are mounted at ends of a pin 404 which pivotally supports one end of the crank 500 in the upper member 100. The crank 500 is generally in the shape of an inverted T pivoted at its lower end 502 by the pin 404. The upper end 504 of the crank 500 fits between the bosses 208 and is pivotally connected to the lower member 200 by a pin 506 extending through the bosses 208 and the upper end 504.

The operation of the second embodiment is substantially the same as that of the first embodiment.

Figure 9:
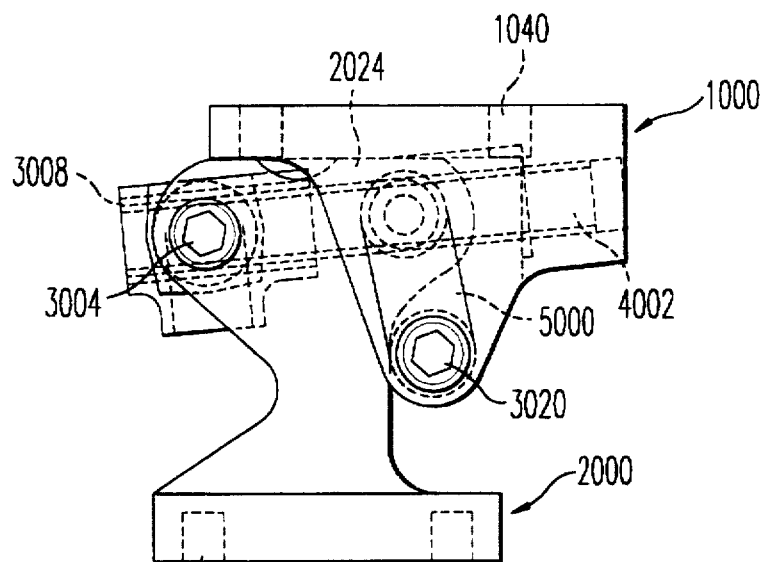
FIG. 9 shows a side elevation of a fully extended knee mechanism of a third embodiment, viewed from the lateral side, with the anterior region to the right of the drawing and the posterior to the left.
Figure 10:
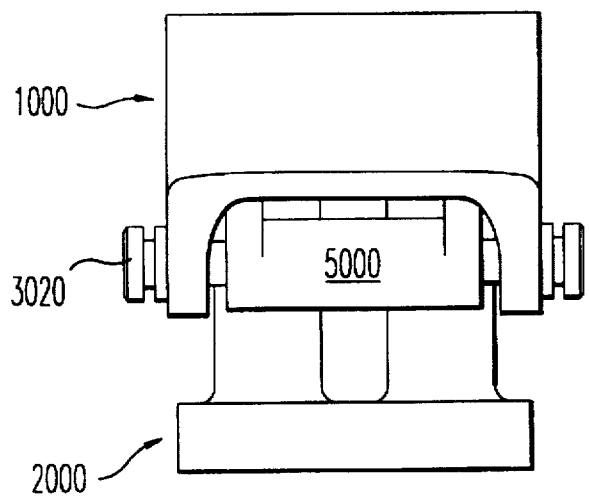
FIG. 10 corresponds to FIG. 3 but shows the third embodiment.
Figure 11:
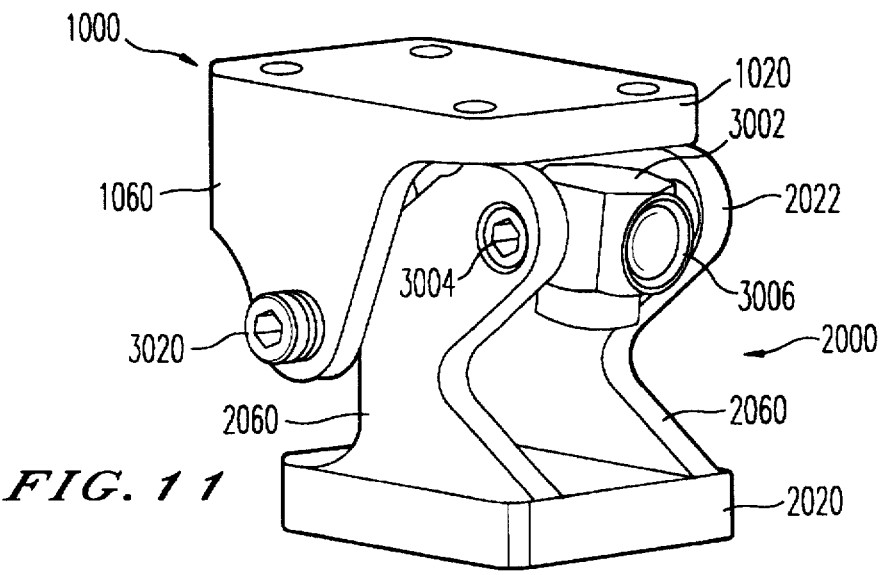
FIG. 11 is a perspective view, from the posterior quarter and from above, of the third embodiment.

Referring now to the third embodiment of FIGS. 9–11, the same reference numbers will be used to designate the same or corresponding parts as those of the first embodiment except that the respective reference numbers will include three additional zeros. The following description will focus on the differences between the embodiments.

The third embodiment is essentially the same as the second embodiment except that it uses a single central track and slider. The track takes the form of a tube or rod 4002, preferably of circular section, rigidly fixed to the underside of the plate 1020 of upper member 1000. The plate 1020 has screw holes 1040. The slider takes the form of a pivoting guide block 3002 pivoted to the lugs 2022 of pedestals 2060 of the lower member 2000 at 3004 and has a central bore 3006 housing a bushing 3008. The bushing may be the model L28 bushing sold by Igus Corp. Of Providence R.I. The bushing 3008 is slidably fitted on the rod 4002 and is guided along the rod as the knee mechanism is articulated.

The crank 5000 is U shaped and is pivoted to the skirts 1006 of the upper member 1000 by pin 3020. It is also pivoted to the lug 2024 of the lower member. The lower member has a rectangular plate 2020.

Obviously, numerous modifications and variations of the present invention are possible in light of the above teachings. It is therefore to be understood that within the scope of the appended claims, the invention may be practiced otherwise than as specifically described herein.

We claim:

1. A knee mechanism in a lower limb prosthesis, comprising:

an upper member connectable to a thigh so as to define a posterior and anterior orientation relative to a load line of the upper member;

a lower member; and a polycentric linkage connecting said lower member to said upper member such that said lower member can rotate posteriorly from a fully extended position with respect to said upper member about an instantaneous center of rotation, wherein said instantaneous center of rotation is above the knee mechanism and posterior to the load line when said lower member is in the fully extended position, and wherein, in at least an initial range of flexion of said lower member from said fully extended position, a locus of said instantaneous center of rotation moves continuously downward and to the posterior, with increased flexion of the lower member.

2. The knee mechanism of claim 1 wherein said locus is a curve which is convex toward the posterior.

3. The knee mechanism of claim 2 wherein said polycentric linkage includes means for resisting torsional loading applied thereto.

4. The knee mechanism of claim 1 wherein said polycentric linkage comprises a slider crank mechanism.

5. The knee mechanism of claim 4 wherein said slider crank mechanism comprises:

a track mounted to said upper member;

a slider pivotally mounted to said lower member and confined by said track to move along said track; and a crank pivotally connected to said upper member and to said lower member.

6. A knee mechanism in a lower limb prosthesis, comprising:

an upper member connectable to a thigh so as to define a posterior and anterior orientation relative to a load line of the upper member;

a lower member; and a polycentric linkage connecting said lower member to said upper member, said polycentric linkage comprising a slider crank mechanism including:

a track mounted to said upper member, a slider pivotally mounted to said lower member and constrained by said track to move in a direction substantially perpendicular to the load line of the upper member, and a crank pivotally connected to said upper member and to said lower member.

7. The knee mechanism of claim 6 wherein said polycentric linkage connects said lower member to said upper member such that said lower member can rotate posteriorly from a fully extended position with respect to said upper member about an instantaneous center of rotation, wherein said instantaneous center of rotation is above the knee mechanism and posterior to the load line when said lower member is in the fully extended position.

8. The knee mechanism of claim 7 wherein the pivotal connection of said slider with said lower member is posterior to the pivotal connection of said crank with said lower member.

9. The knee mechanism of claim 8 wherein said crank extends substantially vertically, and wherein the pivotal connection of said crank with said upper member is below and anterior to the pivotal connection of said crank with said lower member, when said lower member is in a fully extended position.

10. The knee mechanism of claim 6 wherein said crank is shaped to resist torsional loads applied thereto.

11. The knee mechanism of claim 10 wherein said crank is U shaped.

12. The knee mechanism of claim 10 wherein said crank is T shaped.

13. The knee mechanism of claim 6 including an anti-rattle spring engaging said slider.

14. The knee mechanism of claim 6 wherein a portion of said knee mechanism forms a stop preventing rotation of said lower member beyond the fully extended position.

15. The knee mechanism of claim 6 wherein said track is adjustably mounted to said upper member.

16. The knee mechanism of claim 6 wherein a portion of said knee mechanism forms a stop preventing rotation of said lower member beyond a selected flexion position.

17. The knee mechanism of claim 6 wherein said track comprises a rod fixed to said upper member and said slider comprises a guide element pivoted to said lower member and slidably mounted on said rod.

18. A lower limb prosthesis, comprising:

a thigh member;

a shin member;

an upper member connected to the thigh member so as to define a posterior and anterior orientation relative to a load line of the upper member;

a lower member connected to the shin member; and a polycentric linkage connecting said lower member to said upper member such that said lower member can rotate posteriorly from a fully extended position with respect to said upper member about an instantaneous center of rotation, wherein said instantaneous center of rotation is above the knee mechanism and posterior to the load line when said lower member is in the fully extended position, and wherein, in at least an initial range of flexion of said lower member from said fully extended position, a locus of said instantaneous center of rotation moves continuously downward and to the posterior, with increased flexion of the lower member.

19. The prosthesis of claim 18 wherein said locus is a curve which is convex toward the posterior.

20. The prosthesis of claim 19 wherein said polycentric linkage includes means for resisting torsional loading applied thereto.

21. The prosthesis of claim 18 wherein said polycentric linkage comprises a slider crank mechanism.

22. The prosthesis of claim 21 wherein said slider crank mechanism comprises:

a track mounted to said upper member;

a slider pivotally mounted to said lower member and confined by said track to move along said track; and a crank pivotally connected to said upper member and to said lower member.

23. A lower limb prosthesis, comprising:

a thigh member;

a shin member;

an upper member connected to the thigh member so as to define a posterior and anterior orientation relative to a load line of the upper member;

a lower member connected to the shin member; and a polycentric linkage connecting said lower member to said upper member, said polycentric linkage comprising a slider crank mechanism including:

a track mounted to said upper member, a slider pivotally mounted to said lower member and constrained by said track to move in a direction substantially perpendicular to the load line of the upper member, and a crank pivotally connected to said upper member and to said lower member.

24. The prosthesis of claim 23 wherein said polycentric linkage connects said lower member to said upper member such that said lower member can rotate posteriorly from a fully extended position with respect to said upper member about an instantaneous center of rotation, wherein said instantaneous center of rotation is above the knee mechanism and posterior to the load line when said lower member is in the fully extended position.

25. The prosthesis of claim 24 wherein the pivotal connection of said slider with said lower member is posterior to the pivotal connection of said crank with said lower member.

26. The prosthesis of claim 25 wherein said crank extends substantially vertically, and wherein the pivotal connection of said crank with said upper member is below and anterior to the pivotal connection of said crank with said lower member, when said lower member is in a fully extended position.

27. The prosthesis of claim 23 wherein said crank is shaped to resist torsional loads applied thereto.

28. The prosthesis of claim 27 wherein said crank is U shaped.

29. The knee mechanism of claim 27 wherein said crank is T shaped.

30. The knee mechanism of claim 23 including an anti-rattle spring engaging said slider.

31. The prosthesis of claim 23 wherein a portion of said knee mechanism forms a stop preventing rotation of said lower member beyond the fully extended position.

32. The prosthesis of claim 23 wherein said track is adjustably mounted to said upper member.

33. The prosthesis of claim 23 wherein a portion of said knee mechanism forms a stop preventing rotation of said lower member beyond a selected flexion position.

34. The knee mechanism of claim 23 wherein said track comprises a rod fixed to said upper member and said slider comprises a guide element pivoted to said lower member and slidably mounted on said rod.

* * * * *